(12) United States Patent
Sandhu et al.

(10) Patent No.: US 10,925,592 B2
(45) Date of Patent: Feb. 23, 2021

(54) TISSUE DILATION SYSTEM AND METHODS OF USE

(71) Applicant: K2M, Inc., Leesburg, VA (US)

(72) Inventors: Faheem Sandhu, Washington, DC (US); Amjad Anaizi, Washington, DC (US); Scott Koysh, Pittsburgh, PA (US)

(73) Assignee: K2M, Inc., Leesburg, VA (US)

( * ) Notice: Subject to any disclaimer, the term of this patent is extended or adjusted under 35 U.S.C. 154(b) by 257 days.

(21) Appl. No.: 16/071,033

(22) PCT Filed: Jan. 19, 2017

(86) PCT No.: PCT/US2017/014068
§ 371 (c)(1),
(2) Date: Jul. 18, 2018

(87) PCT Pub. No.: WO2017/127502
PCT Pub. Date: Jul. 27, 2017

(65) Prior Publication Data
US 2019/0076172 A1 Mar. 14, 2019

Related U.S. Application Data

(60) Provisional application No. 62/280,198, filed on Jan. 19, 2016.

(51) Int. Cl.
*A61B 17/02* (2006.01)
*A61B 17/34* (2006.01)
(Continued)

(52) U.S. Cl.
CPC .......... *A61B 17/0218* (2013.01); *A61B 17/02* (2013.01); *A61B 17/0206* (2013.01);
(Continued)

(58) Field of Classification Search
CPC ....... A61B 1/32; A61B 17/02; A61B 17/0206; A61B 17/0218; A61B 17/34; A61B 17/3417; A61B 17/3468; A61B 17/3472
See application file for complete search history.

(56) References Cited

U.S. PATENT DOCUMENTS 4,862,891 A * 9/1989 Smith ................. A61B 17/3417
606/191
5,772,678 A * 6/1998 Thomason .......... A61B 17/3417
604/164.1
(Continued)

OTHER PUBLICATIONS

International Search Report and Written Opinion dated Mar. 23, 2017 in corresponding International Application No. PCT/US2017/014068.
(Continued)

*Primary Examiner* — Eric S Gibson
(74) *Attorney, Agent, or Firm* — Lerner, David, Littenberg, Krumholz & Mentlik, LLP

(57) ABSTRACT

Disclosed herein are systems and methods for dilating tissue for placement of a pedicle screw without the use of guide wires. The tissue dilation system includes, generally, a stylet and trocar which are used for the initial placement of the tissue dilation system. A second dilator is passed over the first. A second dilator is passed over the first dilator, and further includes a serrated edge for engaging with a target surface. The second dilator may be secured to the target surface by the serrated edge alone, or may additional be secured using one or more temporary fixation pins, which operably couple to the second dilator.

16 Claims, 21 Drawing Sheets

(51) Int. Cl.
*A61B 17/86* (2006.01)
*A61B 17/70* (2006.01)
*A61B 17/88* (2006.01)

(52) U.S. Cl.
CPC ...... *A61B 17/3468* (2013.01); *A61B 17/7082* (2013.01); *A61B 17/86* (2013.01); *A61B 17/34* (2013.01); *A61B 17/3472* (2013.01); *A61B 17/885* (2013.01)

(56) References Cited

U.S. PATENT DOCUMENTS

| | | | | |
|---|---|---|---|---|
| 6,360,750 | B1* | 3/2002 | Gerber | A61N 1/0551 |
| | | | | 128/898 |
| 6,916,330 | B2* | 7/2005 | Simonson | A61B 17/025 |
| | | | | 606/191 |
| 7,008,431 | B2* | 3/2006 | Simonson | A61B 17/0218 |
| | | | | 606/86 R |
| 7,811,303 | B2* | 10/2010 | Fallin | A61B 17/3417 |
| | | | | 606/191 |
| 8,192,437 | B2* | 6/2012 | Simonson | A61B 17/0218 |
| | | | | 606/86 A |
| 8,834,507 | B2* | 9/2014 | Mire | A61B 17/3421 |
| | | | | 606/191 |
| 8,936,626 | B1* | 1/2015 | Tohmeh | A61B 17/1615 |
| | | | | 606/279 |
| 9,259,213 | B1* | 2/2016 | O'Hara | A61F 2/4611 |
| 9,387,009 | B2* | 7/2016 | Fatone | A61B 5/0492 |
| 9,579,131 | B1* | 2/2017 | Gustine | A61B 17/705 |
| 10,258,228 | B2* | 4/2019 | Genovese | A61B 17/7082 |
| 2003/0083688 | A1* | 5/2003 | Simonson | A61B 1/32 |
| | | | | 606/191 |
| 2003/0083689 | A1* | 5/2003 | Simonson | A61B 17/025 |
| | | | | 606/191 |
| 2004/0059339 | A1* | 3/2004 | Roehm, III | A61B 17/3421 |
| | | | | 606/90 |
| 2004/0138662 | A1* | 7/2004 | Landry | A61B 17/7037 |
| | | | | 606/86 A |
| 2005/0004593 | A1* | 1/2005 | Simonson | A61B 17/025 |
| | | | | 606/191 |
| 2005/0261698 | A1 | 11/2005 | Powell | |
| 2006/0004398 | A1* | 1/2006 | Binder, Jr. | A61M 29/00 |
| | | | | 606/191 |
| 2008/0009826 | A1 | 1/2008 | Miller et al. | |
| 2009/0149857 | A1* | 6/2009 | Culbert | A61B 1/06 |
| | | | | 606/80 |
| 2010/0114147 | A1* | 5/2010 | Biyani | A61B 1/32 |
| | | | | 606/191 |
| 2010/0198271 | A1* | 8/2010 | Leone | A61B 17/7076 |
| | | | | 606/302 |
| 2016/0038195 | A1* | 2/2016 | Genovese | A61B 1/32 |
| | | | | 606/79 |
| 2019/0076172 | A1* | 3/2019 | Sandhu | A61B 17/88 |

OTHER PUBLICATIONS

International Preliminary Report on Patentability dated Aug. 2, 2018 in corresponding International Application No. PCT/US2017/014068.

* cited by examiner

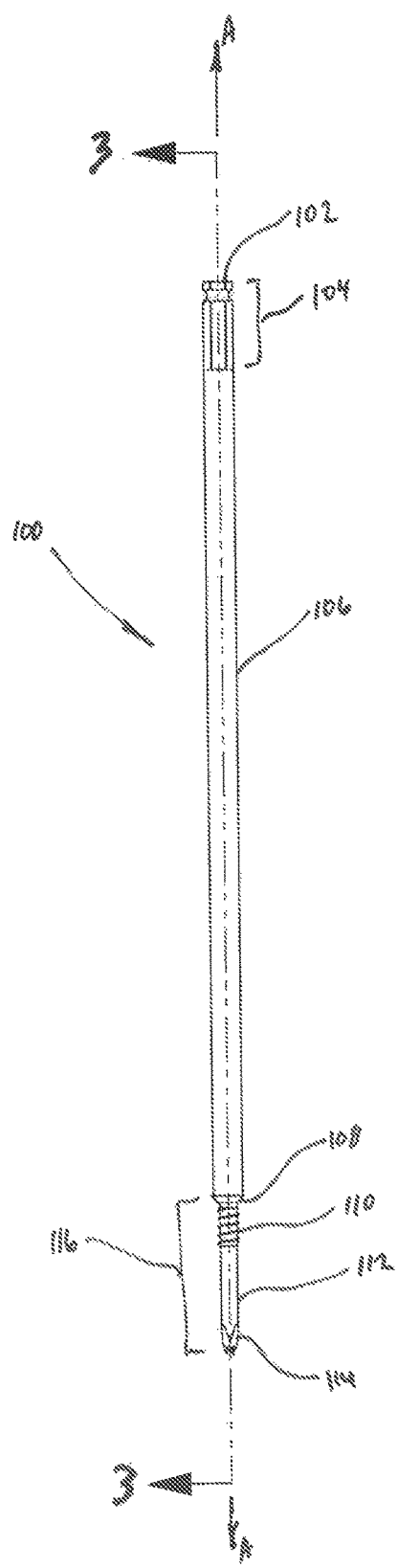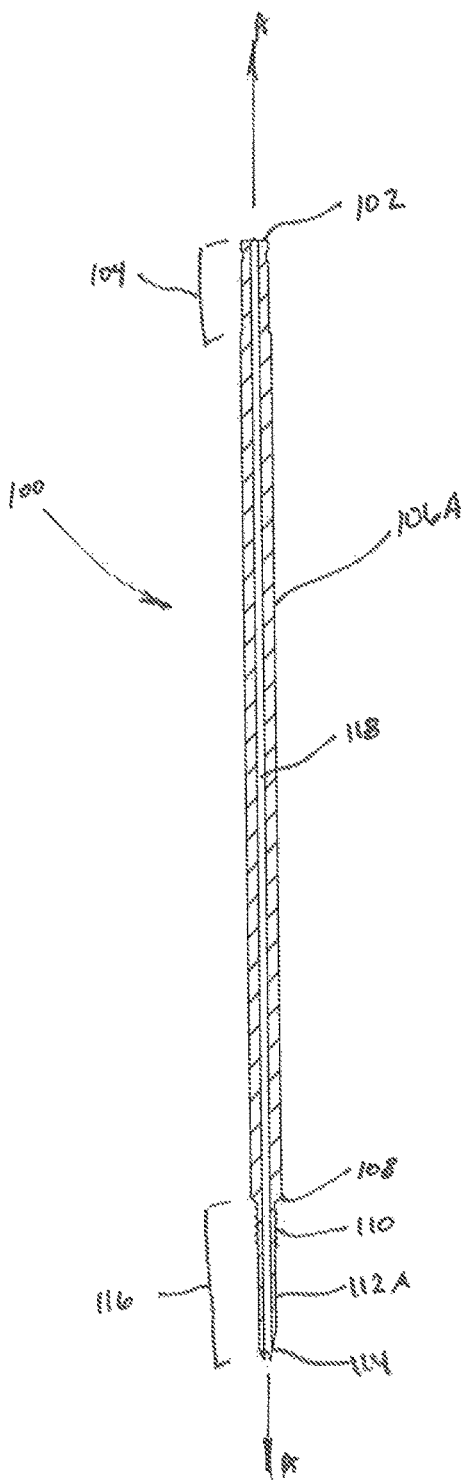
Fig. 2
Fig. 3

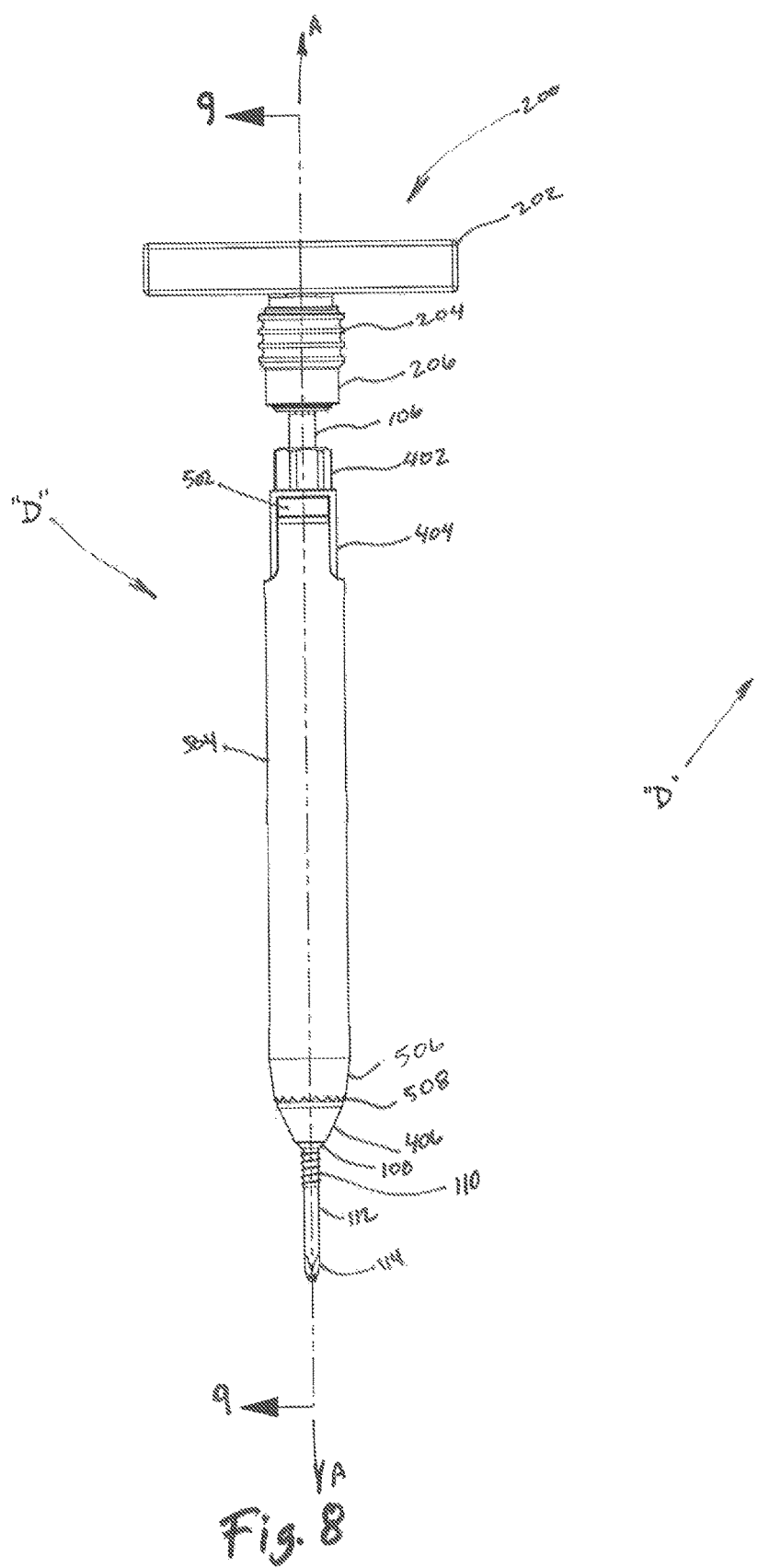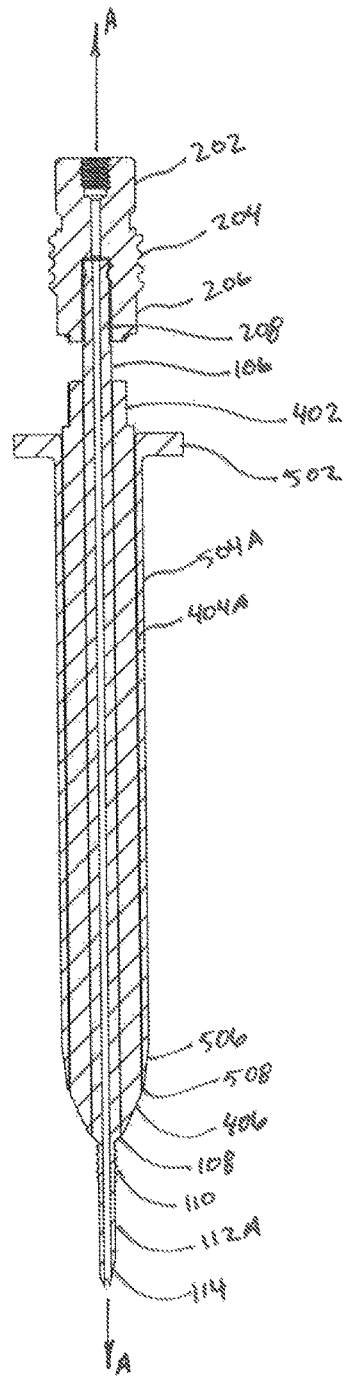

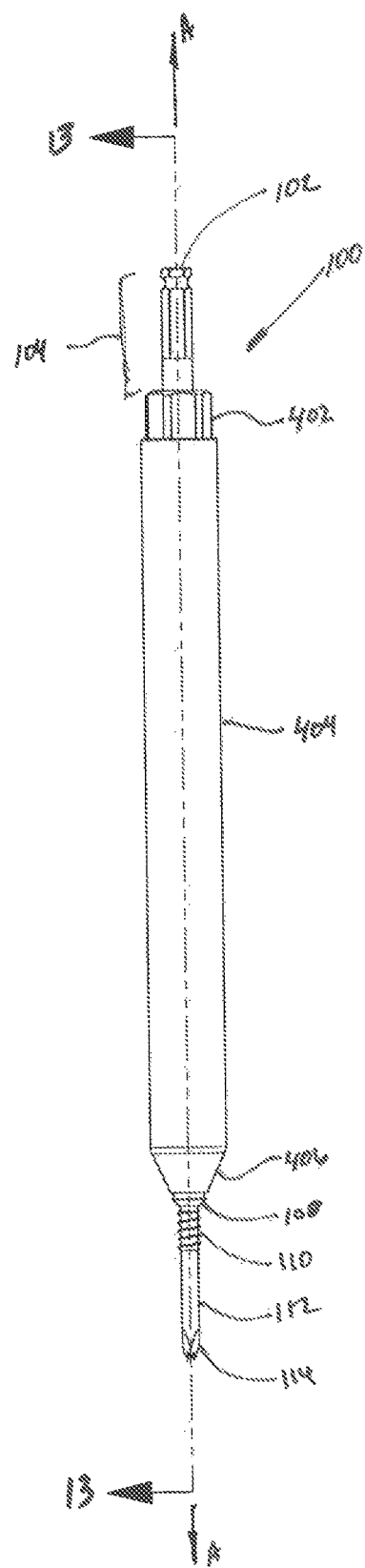
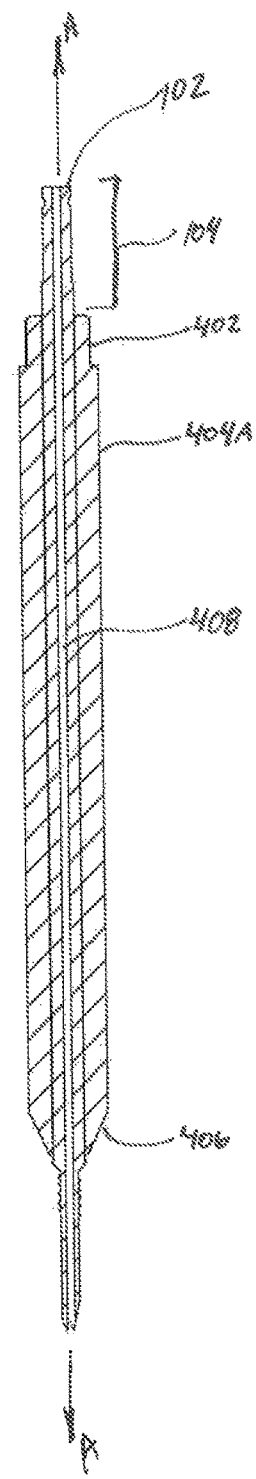
Fig. 12
Fig. 13

TISSUE DILATION SYSTEM AND METHODS OF USE

CROSS-REFERENCE TO RELATED APPLICATION

The present application claims priority to, and the benefit of, U.S. Provisional Application Ser. No. 62/280,198 which was filed on Jan. 19, 2016, the entire contents of which are incorporated by reference herein.

TECHNICAL FIELD

The present disclosure relates to surgical dilation systems. More particularly, the present disclosure relates to a tissue dilation system and methods of use.

BACKGROUND

Development of minimally invasive surgical techniques has expanded to improve orthopedic surgical techniques. Such techniques have advanced the improvement of spinal surgeries, such as instrumental fusions involving one or more vertebral bodies. Unlike minimally invasive procedures which focus on smaller regions of the body, such as arthroscopic knee surgery or gallbladder surgery, spinal fusion surgery can encompass a considerable region of the body.

The spinal column is a complex system of bones and connective tissues that provide support for the human body and protection for the spinal cord and nerves. The adult spinal column is comprised of an upper and lower portion. The upper portion contains twenty-four discrete bones, which are subdivided into three areas including seven cervical vertebrae, twelve thoracic vertebrae and five lumbar vertebrae. The lower portion is comprised of the sacral and coccygeal bones. The cylindrical shaped bones, called vertebral bodies, progressively increase in size from the upper portion downwards to the lower portion.

Minimally-invasive surgery, including arthroscopic surgery and laparoscopic surgery allow for the introduction of fluid (such as liquids or pressurized gasses) for distending tissue and creating working space for the surgeon to operate within. Spinal column surgery does not involve distending tissue to create a cavity in which the surgeon can operate, rather, spinal column surgery often involves interacting with multiple layers of soft tissue, ligaments, nerves, and ultimately bone. For these reasons, the idea of performing minimally invasive orthopedic surgeries has been the focus of many recent medical advances.

Minimally-invasive surgery techniques associated with orthopedic surgery often required a surgeon insert a guide wire through tissue toward a pedicle of the vertebral body. The guide wire thereby enabled the surgeon to accurately attach a pedicle screw to the vertebral body to later secure a rail or rod to the vertebral body. However, during installation, the guide wire may not be inserted to a sufficient depth in the vertebral body, resulting in detachment of the guide wire from the vertebral body prior to insertion of the pedicle screw. Disengagement of the guide wire may result in contamination and necessitate replacement of the guide wire. Additionally, a guide wire may deflect or break during the surgical procedure as a result of catching on a foreign object such as a surgeon's clothing. As a result of deflecting or breaking guide wires, the surgical procedure is prolonged as replacements are fitted as is necessary.

As a result, procedures or surgical instrument improvements associated with guiding pedicle screws to vertebral bodies are desirable.

SUMMARY

The present disclosure relates to a tissue dilation system including a trocar having an elongated body with a bore extending therethrough. A distal region of the elongated body has threads for engaging bone. A stylet is insertable into the bore. The system further includes a first dilator having an elongated body and translatable over an outer surface of the trocar, and an outer dilator having an elongated body and translatable over an outer surface of the first dilator.

The tissue dilation system may further include a handle portion configured to be removably attached to the trocar.

The handle portion may be configured to be removably attached to the first dilator.

The tissue dilation system may further have at least one temporary fixation pin with an elongated body and being translatable along an outer surface of the outer dilator. The temporary fixation pin may have a threaded distal region for engagement with bone.

The outer dilator may be configured to receive a surgical device to be translated within the outer dilator for engaging bone.

A retractor assembly having a retractor and a screw inserter assembly may also be provided.

The retractor assembly may further include a screw and a knob.

The present disclosure also provides a method for dilating tissue including inserting a trocar into a target surface. The trocar has a tubular member with a bore extending between proximal and distal regions thereof. The distal region includes threads for engaging bone. The method further includes coupling a stylet to the trocar such that a distal region of the stylet extends beyond the distal region of the trocar. Bone is contacted at the target surface with the distal region of the trocar. The stylet is separated from the trocar by translating a first dilator over the trocar towards bone at the target surface and translating an outer dilator over the first dilator. The outer dilator is then coupled to bone at the target surface.

The method for dilating tissue may include connecting the trocar with bone at the target surface.

Translating the first dilator over the trocar may include the first dilator having a serrated edge configured to engage with a target surface.

Translating the outer dilator over the first dilator may include the outer dilator having a distal region with a serrated edge configured to engage with a target surface.

Translating the first dilator over the trocar may include the first dilator having a bore configured for slidably receiving the trocar.

Translating the outer dilator over the first dilator may include the outer dilator having a bore configured to engage with an outer surface of the first dilator.

The method for dilating tissue may include removably attaching a handle to either the trocar or the first dilator.

The method for dilating tissue may include coupling the first dilator and the outer dilator prior to translating the first dilator over the trocar towards bone at the target surface.

The method for dilating tissue may include coupling the outer dilator to bone at the target surface by coupling a temporary fixation pin to bone at the target surface, the temporary fixation pin in communication with the outer dilator and having a threaded distal region configured to engage with the target surface.

The method for dilating tissue may include separating the trocar from the target surface.

The method for dilating tissue may include separating the first dilator from the target surface.

BRIEF DESCRIPTION OF THE DRAWINGS

The accompanying drawings illustrate embodiments of the tissue dilation system of the present disclosure.

FIG. 2 is a front plan view of the trocar illustrated in FIG. 1;

FIG. 3 is a cross-sectional view of the trocar of FIG. 2 as taken along section line 3-3 of FIG. 2;

FIG. 8 is a plan view of the tissue dilation system of FIG. 7;

FIG. 9 is a cross-sectional view of the tissue dilation system of FIG. 8 as taken along section line 9-9 of FIG. 8;

FIG. 12 is a front plan view of the trocar and first dilator of FIG. 10;

FIG. 13 is a cross-sectional view of the trocar and first dilator of FIG. 12 taken along section line 13-13 of FIG. 12;

DETAILED DESCRIPTION

Figure 1:
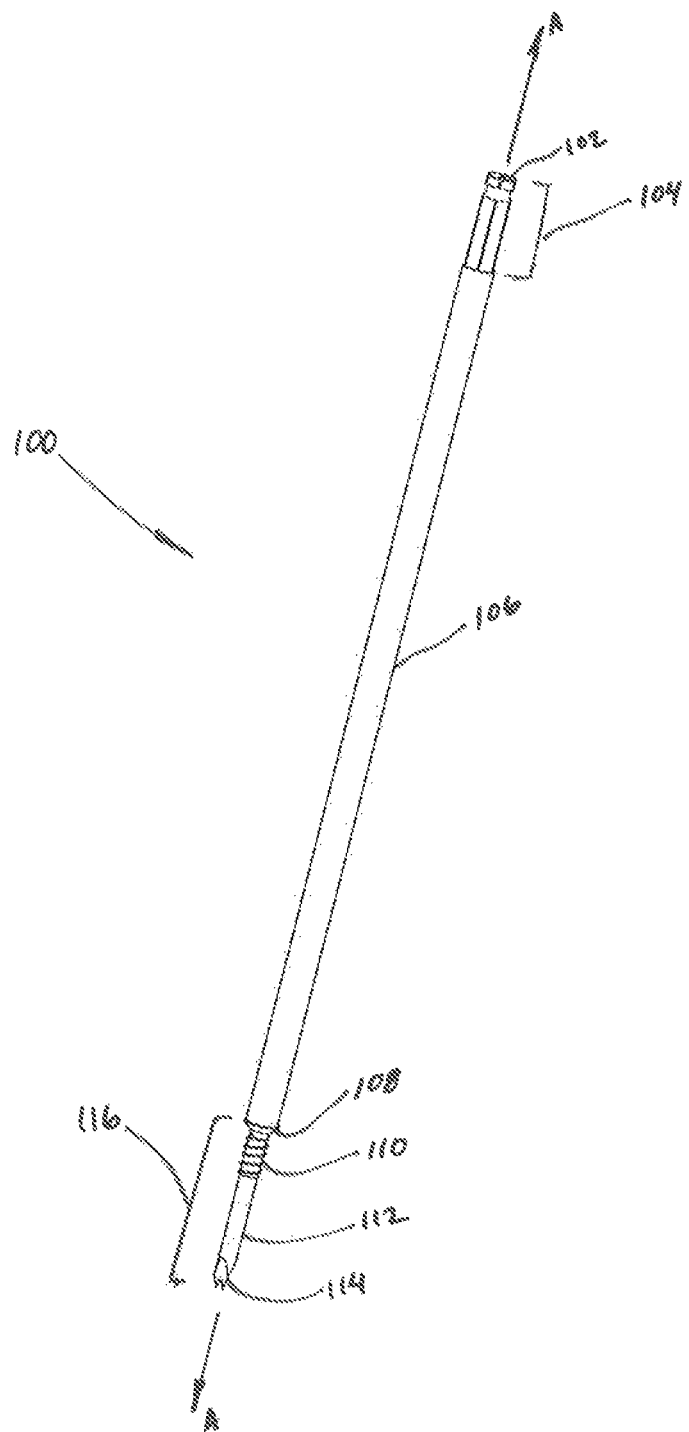
FIG. 1 is a perspective view of a trocar for use in a tissue dilation system.

Embodiments of the present disclosure are described in detail with reference to the drawings, in which like reference numerals designate identical or corresponding elements in each of the several views.

As used herein, the term "distal" refers to the portion of the component being described which is closer to a patient, while the term "proximal" refers to the portion of the component being described which is farther from the patient.

The term "clinician" as used herein refers to a doctor, nurse, healthcare provider which may include support personnel, or other operators of the surgical system described.

Additionally, the positional terms "front," "rear," "top," "bottom," "side," and other like directional terms are used for convenience to assist the reader in understanding the present disclosure, and are not intended to limit the disclosure.

Referring initially to FIG. 1, a trocar 100 is shown including a proximal region 104, a tubular member 106, and a distal region 116. The proximal region 104 includes a proximal end 102 which may be operably coupled to a stylet 300 (see FIGS. 4-6). The proximal region 104 of the trocar 100 may further be dimensioned to receive a handle portion 200 thereon, (see FIG. 4) or other surgical tools (not shown) useful for a dilation procedure.

The tubular member 106 of the trocar 100 extends between the proximal region 104 and the distal region 116 of the trocar 100. The tubular member 106 may be configured and dimensioned for atraumatic advancement through tissue along a longitudinal axis A-A as the trocar 100 is advanced by a clinician toward a target surface (not shown). Likewise, the distal region 116 of the trocar 100 includes a tapered surface 108 located between the tubular member 106 and an engagement member 112 for promotion of atraumatic advancement of the trocar 100 through tissue and operative engagement with an inner dilator 400 (see FIG. 7). The engagement member 112 may include a helical thread, barb, expanding lip, rotated or expanded cam, and other such shaped elements disposed on the outer surface 112A (see FIG. 3) of the engagement member to secure the trocar 100 to the target surface. The engagement member 112 further includes an engagement tip 114 which may include a single or multi-beveled tip for easy viewing via a sub-dermal imaging system as the trocar 100 is advanced toward a target surface.

Referring now to FIGS. 2-3, the trocar 100 includes a bore 118 which extends through the trocar 100 along the longitudinal axis A-A. The bore 118 is dimensioned to slidably receive a stylet 300 (see FIG. 6) therein for selective engagement of the target surface by either a distal tip 308 of the stylet 300 or the engagement tip 114 (see FIG. 6). The bore 118 may be dimensionally defined by an inner surface of the trocar 100.

Figure 4:
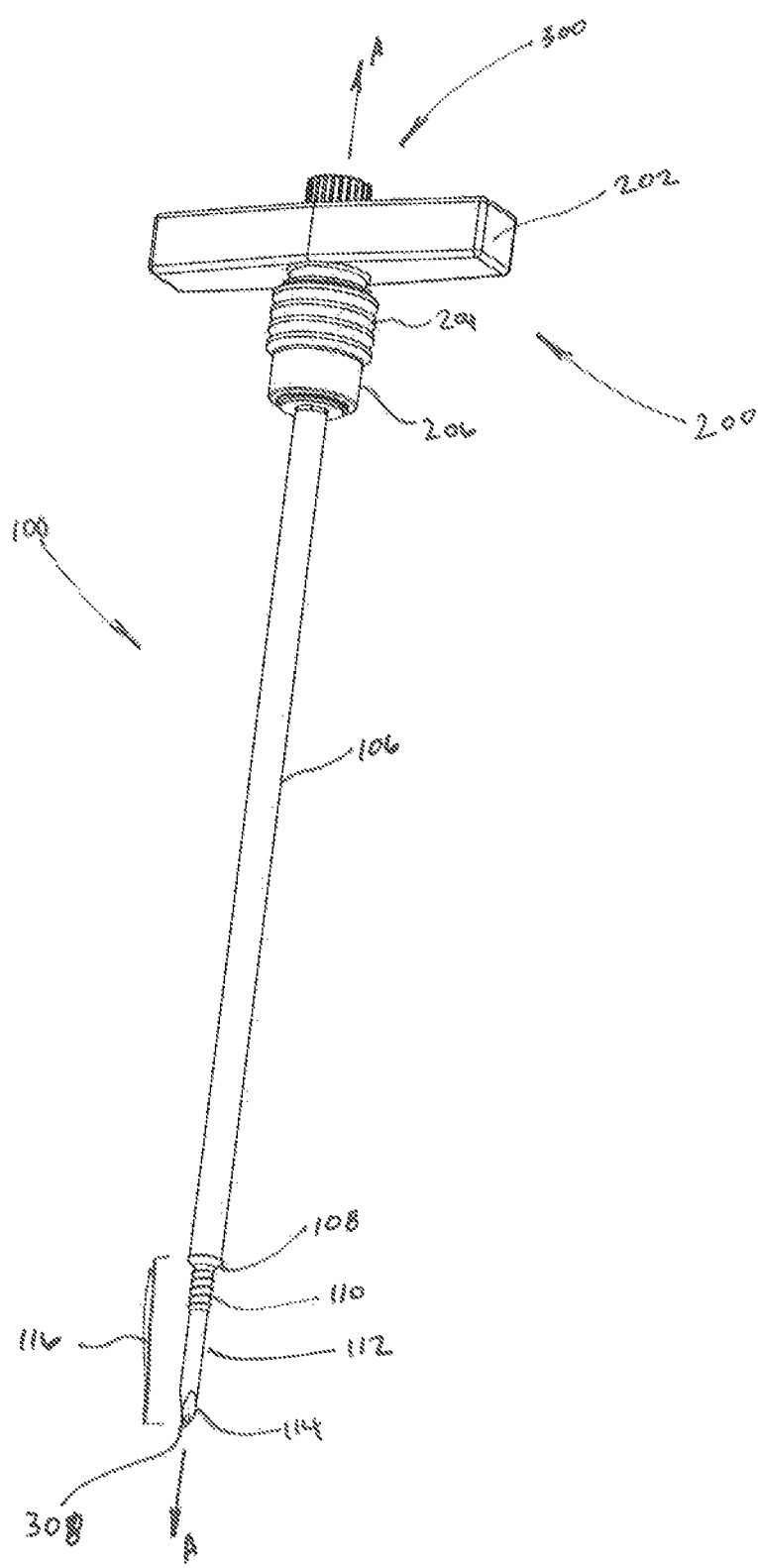
FIG. 4 is a perspective view of the trocar of FIG. 1 attached to a handle portion.
Figure 5:
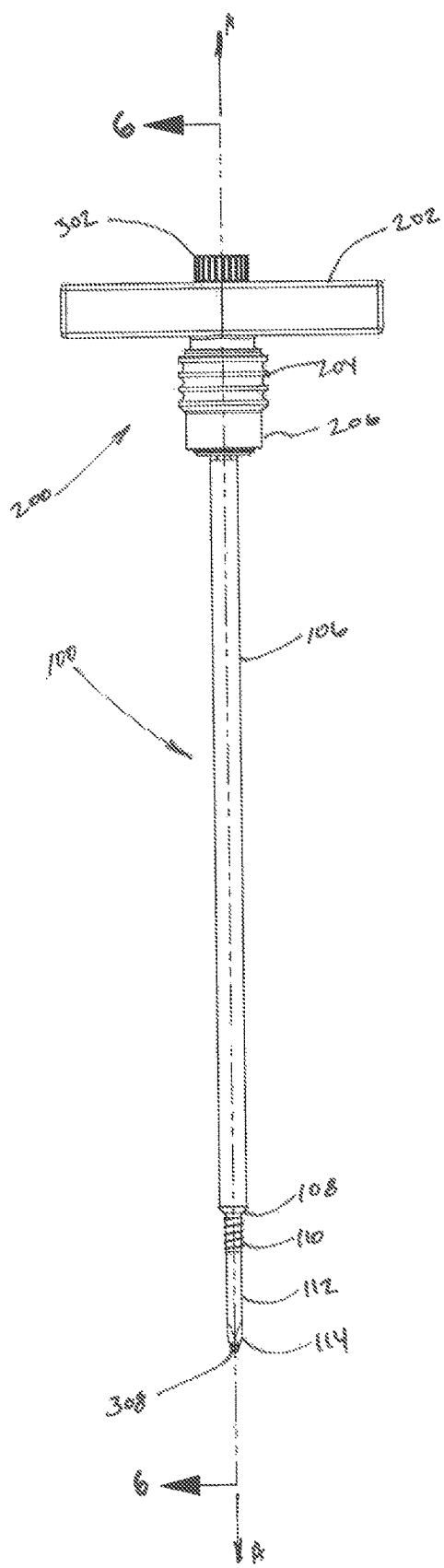
FIG. 5 is a front plan view of the trocar and handle portion of FIG. 4.
Figure 6:
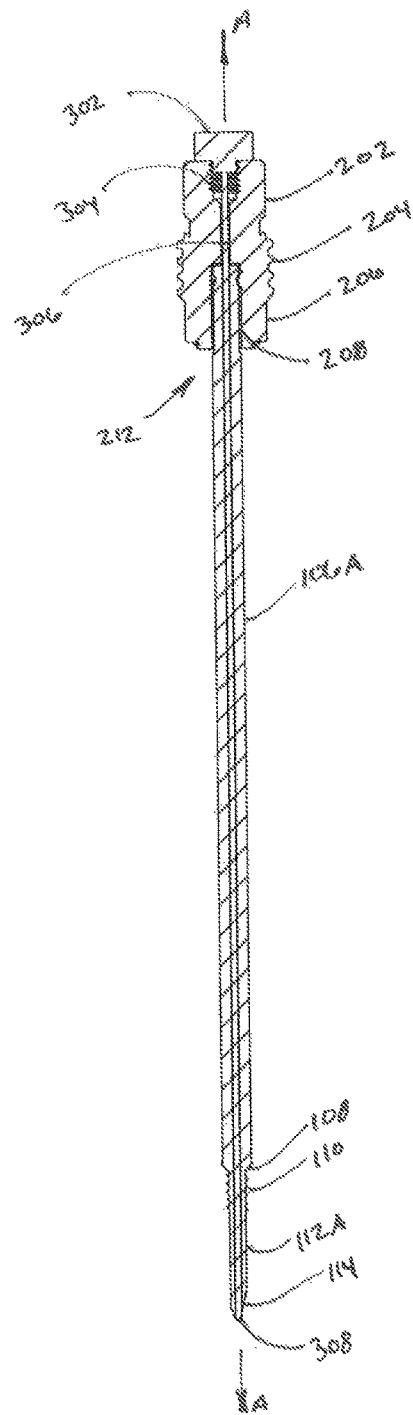
FIG. 6 is a cross-sectional view of the trocar and handle portion of FIG. 5 taken along section line 6-6 of FIG. 5.

Referring now to FIGS. 4-6, the trocar 100 is shown in combination with a handle portion 200 and a stylet 300. The handle portion 200 includes a handle member 202 which is capable of being gripped by a clinician's hand. The handle portion 200 may further include an extension 206 with one or more flanges 204 disposed thereon for engagement by a clinician about the longitudinal axis A-A during assembly and removal of the handle portion 200 from the trocar 100. An engagement surface 208 may be located in the distal region of the handle portion 200, defining a cavity 212 therein. The cavity 212 may be dimensioned to fixably receive the proximal region 104 of the trocar 100. Additionally, the cavity 212 and the proximal region 104 of the trocar 100 may be dimensioned to transfer rotational or torsional force from the handle portion 200 to the trocar 100. The cavity 212 and proximal region 104 of the trocar may be shaped in a variety of ways, including two or more sided shapes, asymmetrical shapes, or patterned shapes that are complementary such that cavity 212 is rotatably coupled with the proximal region 104 and removably coupled to the trocar 100.

With continued reference to FIGS. 4-6, the handle portion 200 and trocar 100 may be combined with a stylet 300. The stylet 300 includes a knob 302 having a knurled surface which may be gripped by a clinician. The knob 302 may further include threads 304 which operably engage threads 210 of the handle portion 200 for releasably coupling the stylet 300 and the handle portion 200. The stylet 300 further includes a shaft 306 extending from the knob 302, with the shaft 306 being configured and dimensioned for slidably engaging the bore 118 of the trocar 100. Further still, the shaft 306 may be dimensioned such that when the stylet 300 is threadably coupled with the handle portion 200, the distal tip 308 of the shaft 306 extends beyond a distal end of the engagement tip 114 of the trocar 100.

Handle portion 200 may engage with trocar 100 via a spring collet (not shown). In the fixed position, the spring collet associated with handle portion 200 includes ball bearings which are located between the handle portion 200 and the trocar 100. The ball bearings apply pressure against the trocar 100, thereby maintaining the position of the handle portion 200 relative to the trocar 100. To remove the handle portion 200, the clinician applies upward force (i.e., proximal movement) to the handle portion 202 relative to the flanges 204. By pulling the handle portion 202 proximally relative to the flanges 204, the pressure applied to the ball bearings is reduced, thereby allowing the clinician to remove the handle 200. The handle 200 is releasably coupled with the trocar 100 by releasing the handle portion 202, thereby applying pressure against the ball bearings and trocar 100. Alternatively, it is contemplated that the reverse arrangement may be employed where proximal movement of the flanges 204 relative to the handle portion 202 release pressure against the ball bearings allowing the handle 200 to be separated from the trocar 100.

Figure 7:
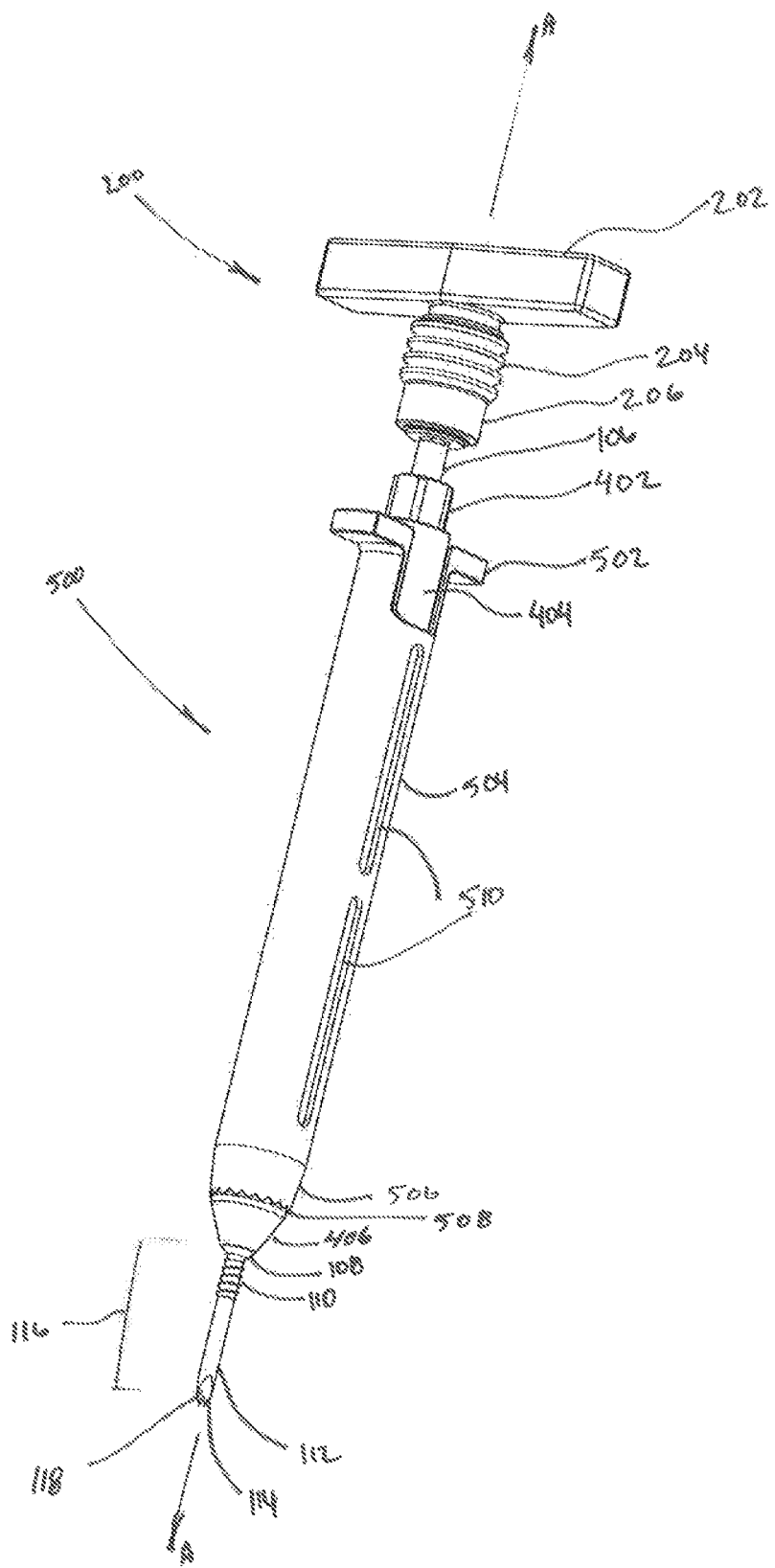
FIG. 7 is a perspective view of a tissue dilation system according to the present disclosure.

Referring now to FIGS. 7-9, a tissue dilation system "D" is shown with the trocar 100, the handle portion 200, an inner dilator 400, and an outer dilator 500. As shown, in combination, the handle portion 200 attaches to the trocar 100. When the handle portion 200 is removed from the trocar 100, the inner dilator 400 may be passed over the trocar 100, and the outer dilator 500 may be passed over the inner dilator 400. The inner dilator 400 may be dimensioned to selectively engage with the trocar 100 or the outer dilator 500 during assembly of the tissue dilation system "D" during a surgical dilation procedure.

Figure 10:
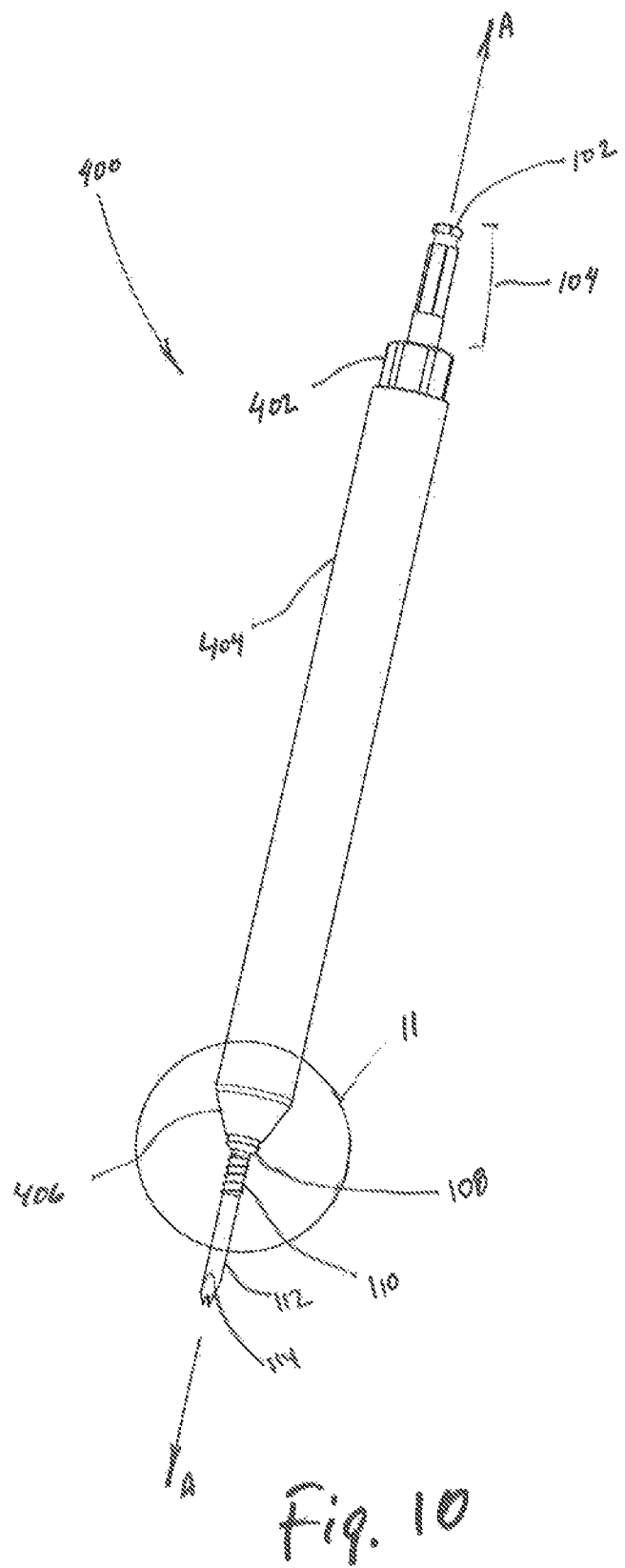
FIG. 10 is a perspective view of the trocar of FIG. 1 and a first dilator according to the present disclosure.

With additional reference to FIG. 10, the inner dilator 400 includes a receiving portion 402, a tubular member 404, a tapered surface 406, and a bore 408 (see FIG. 13). The receiving portion 402 may be dimensioned to engage with a surgical tool (not shown) during the dilation procedure, the surgical tool permitting the clinician to apply force distally against the inner dilator 400. Engagement of the receiving portion 402 with the surgical tool assists the clinician while advancing inner dilator 400 through tissue where the application of additional distal force is desired. The tubular member 404 extends between a proximal and distal region of the inner dilator 400 along longitudinal axis A-A defining the bore 408 therethrough. The tubular member 404 further includes a tapered surface 406 located in the distal region of the inner dilator 400 for atraumatically displacing tissue while the inner dilator 400 is advanced toward the target surface.

With continued reference to FIGS. 7-9, the outer dilator 500 includes two flanges 502 for a clinician to grip during the dilation procedure. The flanges 502 extend from the tubular member 504 of the outer dilator 500 in the proximal region of the tubular member 504. The tubular member 504 may have one or more openings 510 located thereon, allowing a clinician to view a bore 518 defined through the tubular member 504. The bore 518 of the outer dilator 500 is dimensioned to permit the outer dilator 500 to be passed over the inner dilator 400 such that the inner dilator 400 extends therethrough. Further, a clinician can view the progression of the outer dilator 500 over the inner dilator 400 through the one or more openings 510 of the outer dilator 500.

Both the inner dilator 400 and the outer dilator 500 include tapered surfaces 406, 506 dimensioned to minimize unintentional engagement of tissue surrounding or located at the target surface by a clinician during the dilation procedure. The tapered surface 406, 506 of both the inner dilator 400 and outer dilator 500 gradually displace tissue as the inner dilator 400 or outer dilator 500 is advanced through tissue during the dilation procedure toward the target surface.

The outer dilator 500 may further include a serrated edge 508 located on the distal end of the outer dilator 500. The serrated edge 508 provides a surface for rigid connection with bone or other target tissue along a target surface. By including serrated edge 508, outer dilator 500 may be positioned relative to the bone or other target tissue with or without additionally securing the outer dilator 500 to the target surface prior to advancement of a retractor assembly 600 through the outer dilator 500.

With reference to FIG. 9, the cross-section of tissue dilation system "D" shows, in combination, the trocar 100, inner dilator 400, outer dilator 500, and handle portion 200. As the inner dilator 400 is advanced over the trocar 100, the inner dilator 400 is positionally maintained relative to the target surface by the trocar 100 with the inner surface of the inner dilator 400 slidably engaging with the outer surface 106A of the trocar 100. Likewise, as the outer dilator 500 is advanced over the inner dilator 400, the outer dilator 500 is positionally maintained relative to the target surface by the inner dilator 400 with the inner surface of the outer dilator 500 slidably engaging with the outer surface 404A of the inner dilator 400. Once the outer dilator 500 is advanced and engaged with the target surface, both the inner dilator 400 and the trocar 100 may be removed from the tissue dilation system "D" to allow for placement of a pedicle screw at the target surface via the outer dilator 500.

While a tissue dilation procedure has been described in terms of sequential placement of an inner dilator 400 and outer dilator 500 over a trocar 100 toward a target surface, it is contemplated that, depending on the circumstances of the dilation procedure, the trocar 100 may be combined with the inner dilator 400, the inner dilator may be combined with the outer dilator 500, or the trocar 100, the inner dilator 400, and the outer dilator 500 may all be combined prior to advancement through tissue toward a target surface during the dilation procedure.

Referring now to FIG. 10, the trocar 100 is shown in combination with the inner dilator 400. During combination of the trocar 100 the inner dilator 400, the inner dilator 400 is advanced over the trocar 100, thereby displacing tissue as the inner dilator 400 is advanced toward a target surface. The inner dilator 400 may further be engaged at the receiving portion 402 with a surgical tool (not shown) during the dilation procedure. The inner dilator 400 includes a tubular member 404 with the bore 408 dimensioned to pass over the trocar 100, and an outer surface 404A dimensioned to slidably engage with inner surface of the outer dilator 500 (see FIG. 7) therealong. The inner dilator 400 further includes a tapered surface 406 which is dimensioned to engage the distal region 116 of the trocar 100 (see FIG. 11).

Figure 11:
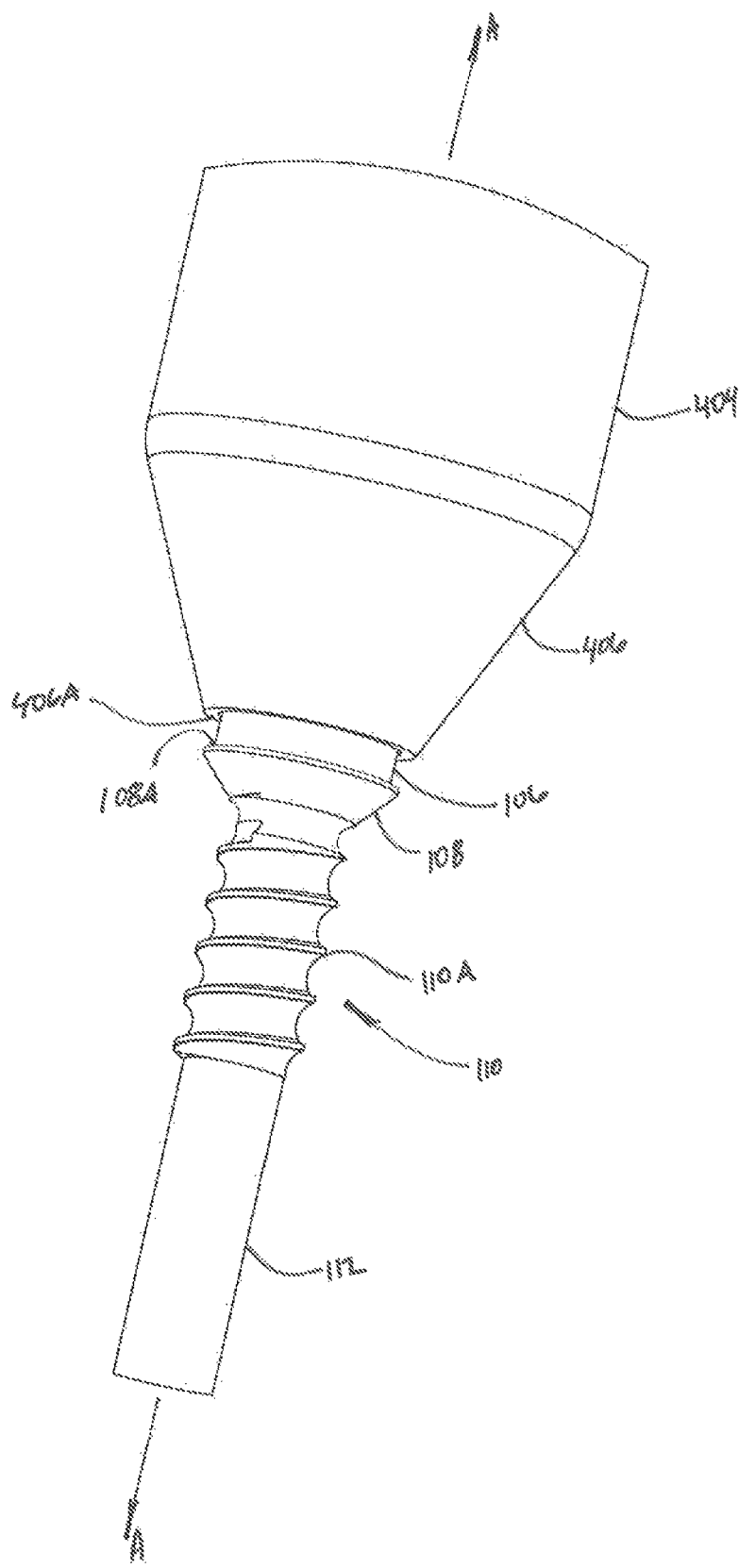
FIG. 11 is enlarged view of the area of detail of FIG. 10.

Referring now to FIG. 11, the distal region of the inner dilator 400 includes an inner dilator end 406A dimensioned to abut a tapered surface flange 108A of the trocar 100. The inner dilator end 406A is located at the proximal-most region of the inner dilator 400 and comes into contact with the tapered surface flange 108A of the trocar 100 as the inner dilator 400 is advanced toward the target surface. Contact between the tapered surface flange 108A and the inner dilator end 406A limits distal advancement of the inner dilator 400 through tissue toward the target surface. It is contemplated that, in alternative embodiments, the tapered surface flange 108A of the trocar 100 may be dimensioned so as to allow the inner dilator 400 to advance toward the target surface. Additionally, the inner dilator 400 may have an inner dilator end 406A which is serrated for engaging with bone at a target surface.

Referring to FIGS. 12-13, the trocar 100 is shown in combination with the inner dilator 400 of FIG. 10. The bore 118 of the trocar 100, as shown in FIG. 13, defines a lumen therethrough within the trocar 100.

Figure 14:
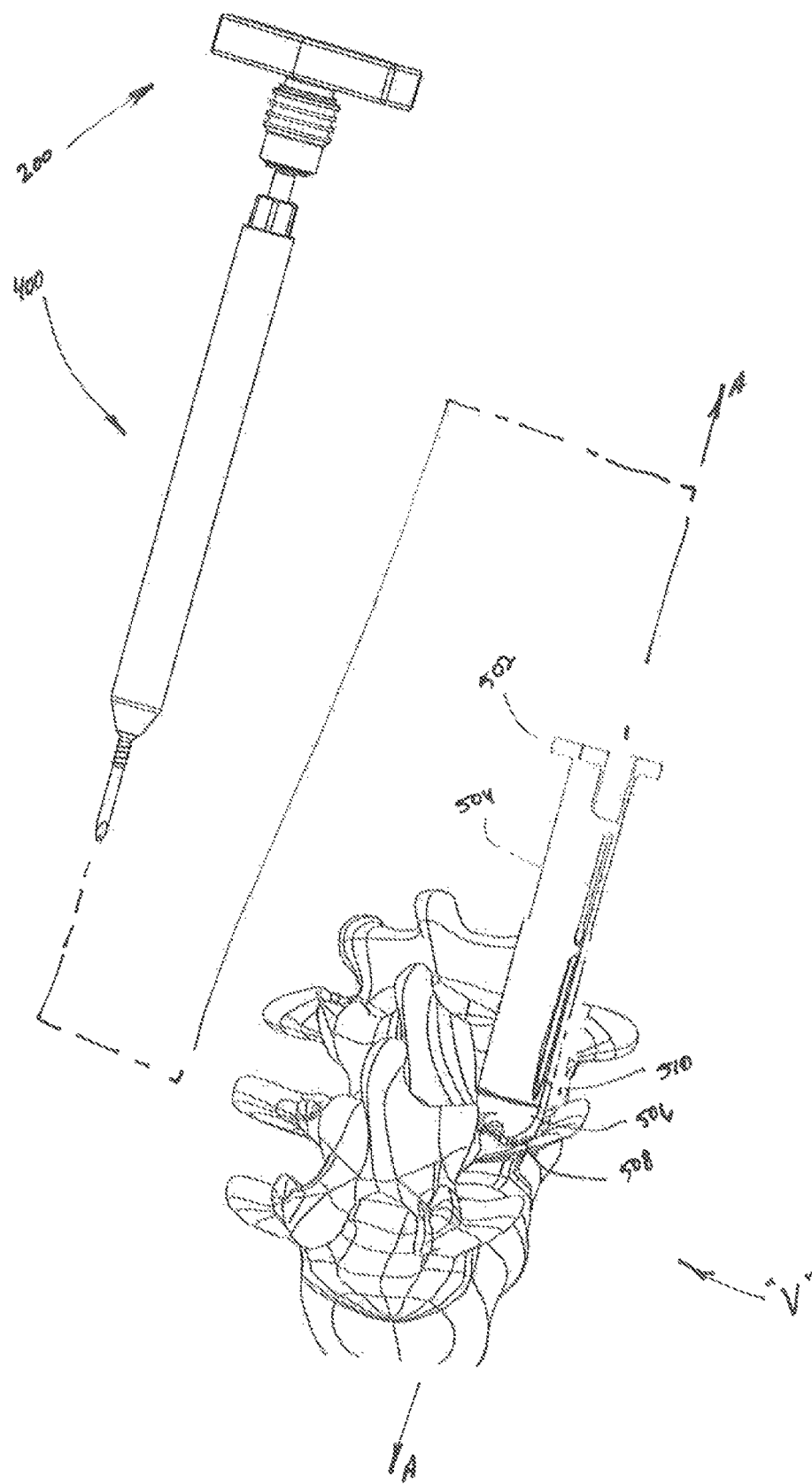
FIG. 14 is an exploded view, with parts separated, of an alternate embodiment of a tissue dilation system according to the present disclosure.

Referring to FIG. 14, the handle portion 200, trocar 100 and inner dilator 400 are shown separated from the outer dilator 500. In an embodiment of the present disclosure, after the outer dilator 500 is advanced toward the target surface and secured via serrated edge 508 to target tissue, the inner dilator 400 and trocar 100 may be removed from the tissue dilation system "D", with the outer dilator 500 remaining connected to target tissue at the target surface. To remove the inner dilator and the trocar 100, a clinician may grip the handle member 202 of the handle portion 200 and apply force proximally relative to the target surface to remove the trocar 100. A step (not shown) is located at a distal end of the trocar 100 that engages the inner dilator 400 such that the trocar 100 and inner dilator 400 can be removed together. Alternatively, the clinician may apply pressure proximally to the flanges 502 of the outer dilator 500, thereby maintaining pressure against the outer dilator 500 and preventing dislodgement of the outer dilator 500 from the target surface as the inner dilator 400 and trocar 100 are removed from the tissue dilation system "D".

Referring to FIGS. 15-18, a retractor assembly 600 may be slidably inserted into the bore 518 of the outer dilator 500 to advance a screw "S" toward a target surface. The retractor assembly 600 includes a screw inserter assembly 604, a knob 602, a retractor collar 608, a retractor 610, and a screw "S".

The knob 602 may include one or more flanges for a clinician to grip during the placement of a screw "S". It is contemplated that the knob 602 may be replaced with a variety of alternative rotational force application mechanisms, designs of which will be apparent to one skilled in the art. The knob 602 is located in a proximal region 614 of the screw inserter assembly 604 and is dimensioned to receive handle portion 200 (see FIG. 4) thereon.

The screw inserter assembly 604 may further include one or more openings 606 located along its surface. The openings 606 may be selectively located so as to promote engagement with varying surgical instruments (not shown) during the dilation and a screw "S" placement procedure. The screw inserter assembly 604 is dimensioned to be slidably assembled with the retractor collar 608 and the retractor 610. The retractor collar 608 may further be dimensioned to enclose a proximal region of the retractor 610, thereby preventing maintaining blades of the retractor 610 in a fixed position.

For a detailed description of a retractor assembly 600, reference may be made to U.S. Pat. No. 8,246,538 entitled "Minimally Invasive Retractor with Separable Blades and Method of Use," and U.S. Pat. No. 8,734,338 entitled "Minimally Invasive retractor and Methods of Use," the entire disclosures of which are incorporated herein by reference.

Figure 15:
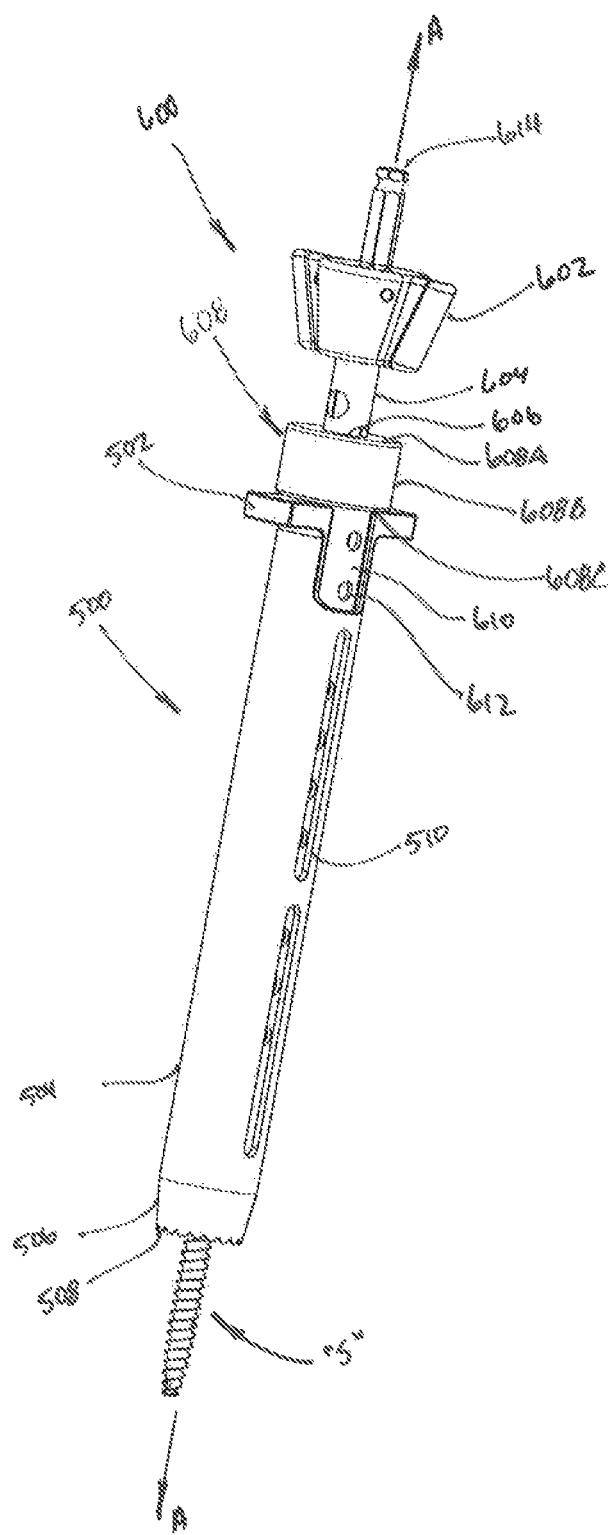
FIG. 15 is a perspective view of a further embodiment of a tissue dilation system according to the present disclosure.

Referring to FIG. 15, the retractor assembly 600 is shown in combination with an outer dilator 500 (see FIG. 7). A retractor collar 608 is dimensioned to abut flange 502 for selective detachment of the retractor 610 from the retractor collar 608 as the retractor assembly 600 is advanced toward the target surface. It is contemplated that the retractor collar 608 may be dimensioned so as to be slidably inserted into the bore 518 of the outer dilator 500 while advancing the retractor assembly 600 toward the target surface. The retractor collar 608 further includes an inner surface 608A and an outer surface 608B, with the inner surface 608A being dimensioned to receive a retractor 610 during assembly therein (see FIG. 19).

Figure 16:
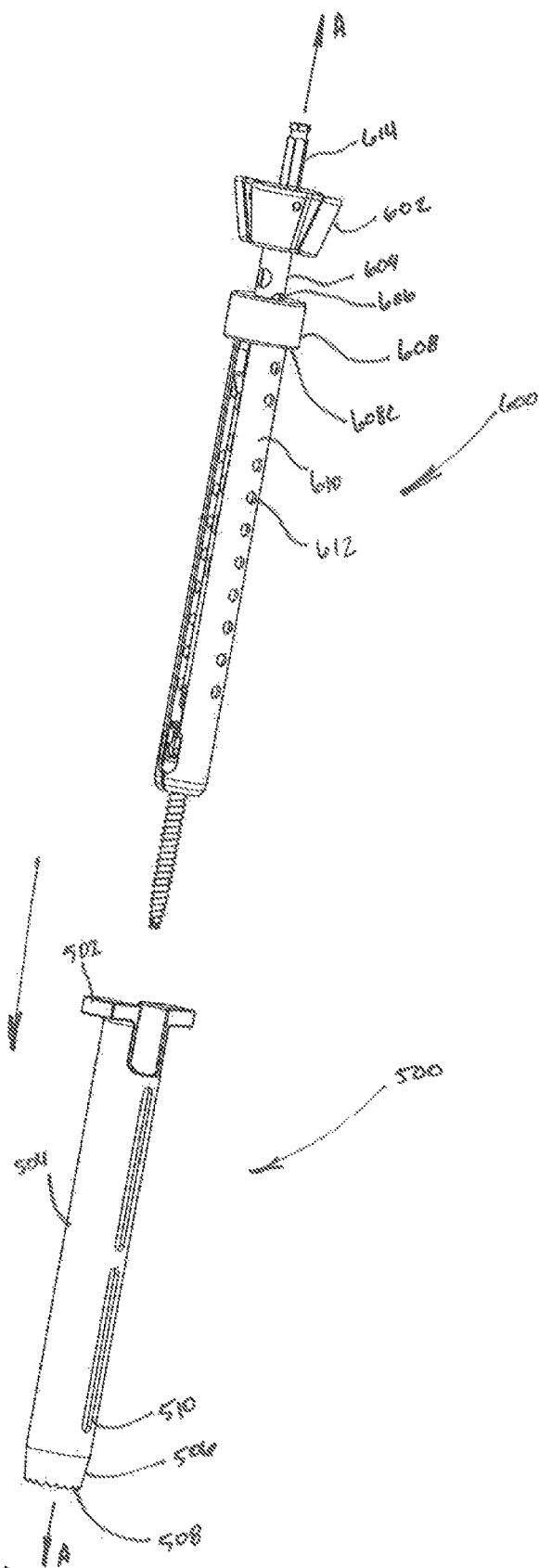
FIG. 16 is an exploded view, with parts separated, of the tissue dilation system of FIG. 15.
Figure 17:
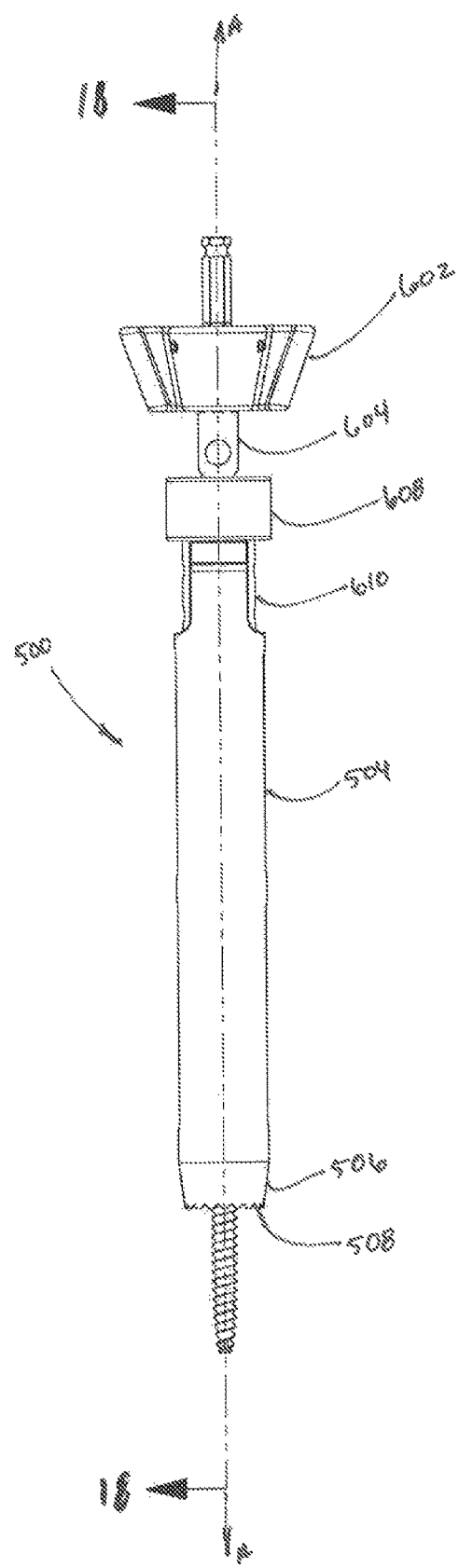
FIG. 17 is a side elevation view of the tissue dilation system of FIG. 15.
Figure 18:
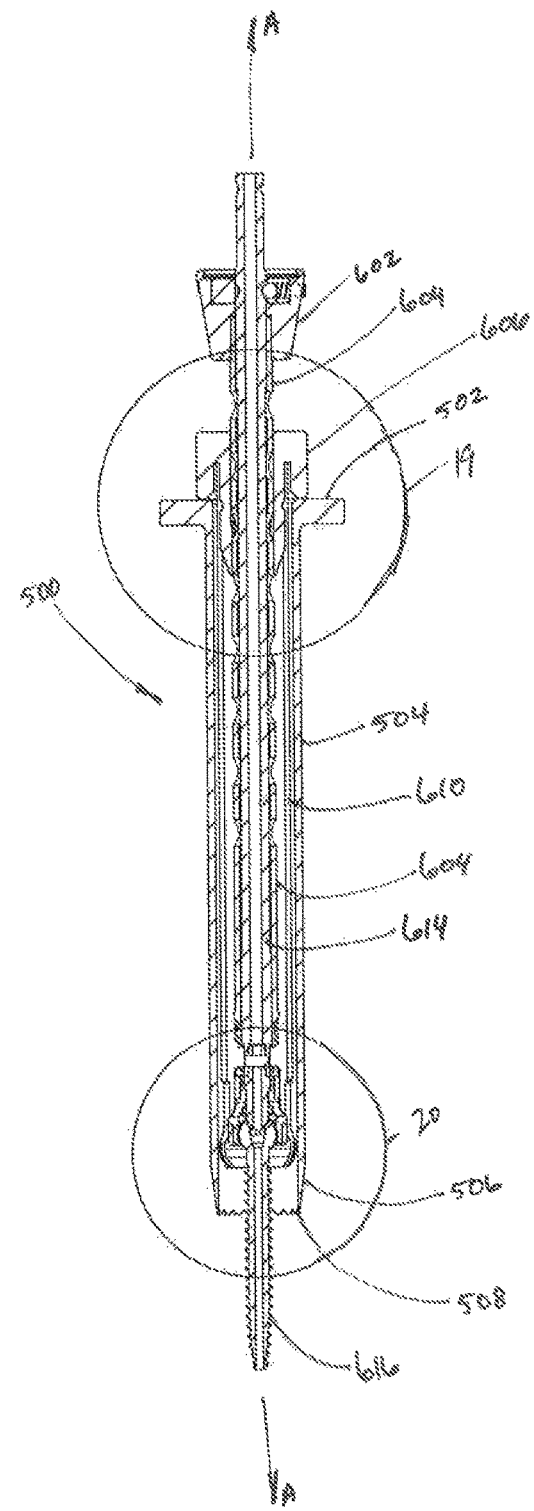
FIG. 18 is a cross-sectional view of the tissue dilation system of FIG. 17 taken along section line 18-18 of FIG. 17.

Referring to FIG. 16, in use the retractor assembly 600 is advanced through a bore 518 of the outer dilator 500, with the outer dilator 500 being fixed to a target surface. Prior to insertion, the clinician assembles screw "S" to the distal region of the screw inserter assembly 604. During assembly, the clinician slides the retractor 610 over the screw "S" and the screw inserter assembly 604, thereby advancing the retractor 610 toward the proximal region of the retractor assembly 600. The clinician also attaches knob 602 to the retractor assembly 600. In combination, the clinician may advance the retractor assembly 600 through the bore 518 of the outer dilator 500 advancing from the proximal region of the outer dilator 500 to the distal region of the outer dilator 500 toward a target surface.

Referring to FIGS. 17-20, the retractor assembly 600 is shown in combination with the outer dilator 500. In a contemplated embodiment, upon assembly the retractor collar 608 secures the proximal portion of the retractor assembly 600 along a proximal region of the bore 518 of outer dilator 500. Additionally, the screw "S" may be engaged by an engagement portion 618 of the screw inserter assembly 604 (see FIG. 20), with both the screw inserter assembly 604 and screw "S" providing outward force to secure the retractor 610 at a distal region of the bore 518 of the outer dilator 500 therein.

Figure 19:
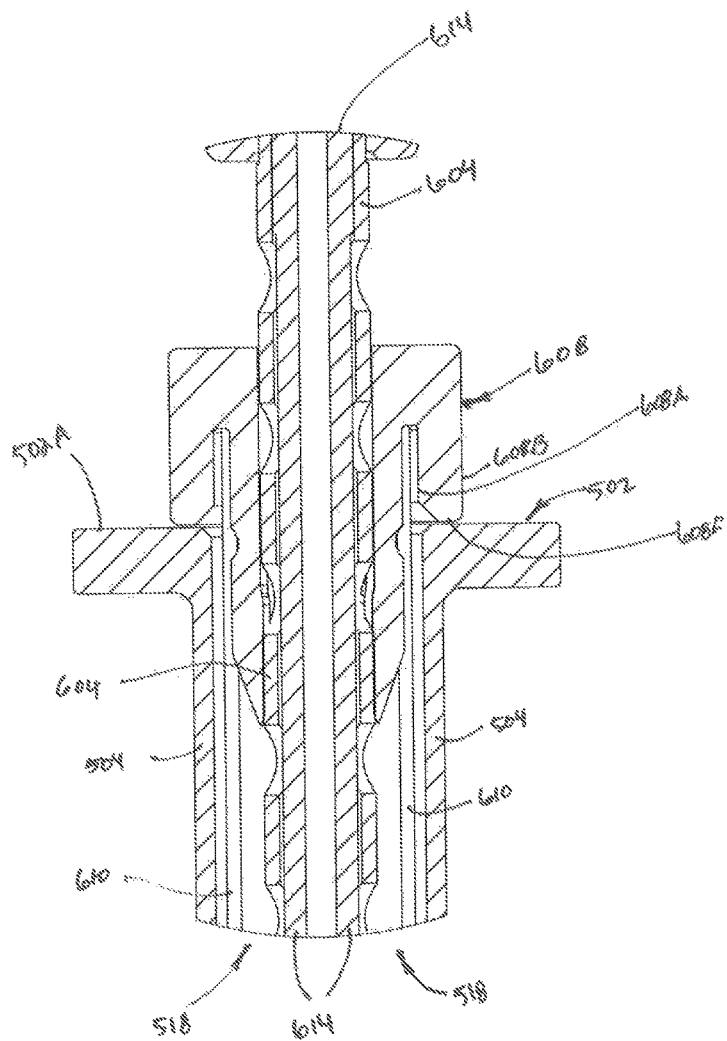
FIG. 19 is an enlarged view of the area of detail of FIG. 18.

Referring to FIG. 19, the retractor collar 608 includes a distal collar surface 608F which, when combined with the retractor assembly 600 (see FIG. 15) abuts flange 502 of the outer dilator 500. As a clinician advances the retractor assembly 600 beyond a predetermined point, the clinician may dislodge the retractor 610 from the retractor collar 608. Once dislodged, the retractor collar 608 may maintain position in the bore 518 of the outer dilator 500 to stabilize the retractor assembly 600 as the retractor assembly 600 is advanced toward the target surface. To remove the outer dilator 500 from the surgical site, the clinician may apply force proximal relative to the target surface to dislodge the outer dilator 500 from the target surface.

Figure 20:
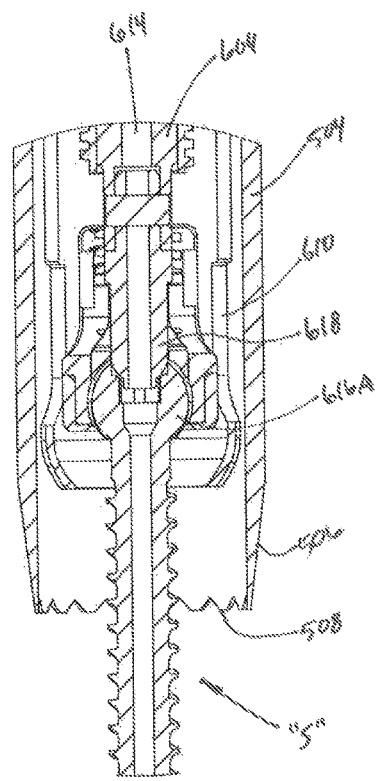
FIG. 20 is an enlarged view of the area of detail of FIG. 18.

Referring to FIG. 20, engagement portion 618 may further include engagement tip 618A dimensioned to engage screw head 616A. As a result of the mating of the engagement tip 618A with the screw head 616A, rotation of the screw inserter assembly 604 rotates the screw "S" for insertion into or removal from target tissue (i.e., bone). After placing the screw "S" into target tissue, the clinician may apply sufficient force to screw inserter assembly 604 proximally or away from screw "S" to the screw inserter assembly 604, thereby dislodging the screw inserter assembly 604 from the screw "S" and the retractor 610. If the clinician determines it necessary to remove screw inserter assembly 604 while leaving retractor 610 in position, the surgeon may apply force as is necessary to dislodge the screw inserter assembly 604 from the retractor collar 608, thereby maintaining the position of the retractor collar 608 and the retractor 610, relative to screw "S".

With continued reference to FIG. 20, a distal region 620 of the retractor 610 may be shaped so as to require force to dislodge the retractor 610 from the screw "S". Upon removal of the screw inserter assembly 604, the retractor 610 may contract around the screw head 616A. It is contemplated that retractor 610 may be made of a pliable, biocompatible, and sterilizable material such as polypropylene, polyethylene, or polycarbonate. By including pliable, biocompatible, and sterilizable materials, the retractor 610 may be deformed at the distal retractor end 620 as the retractor 610 is slid over the screw head 616A.

Figure 21:
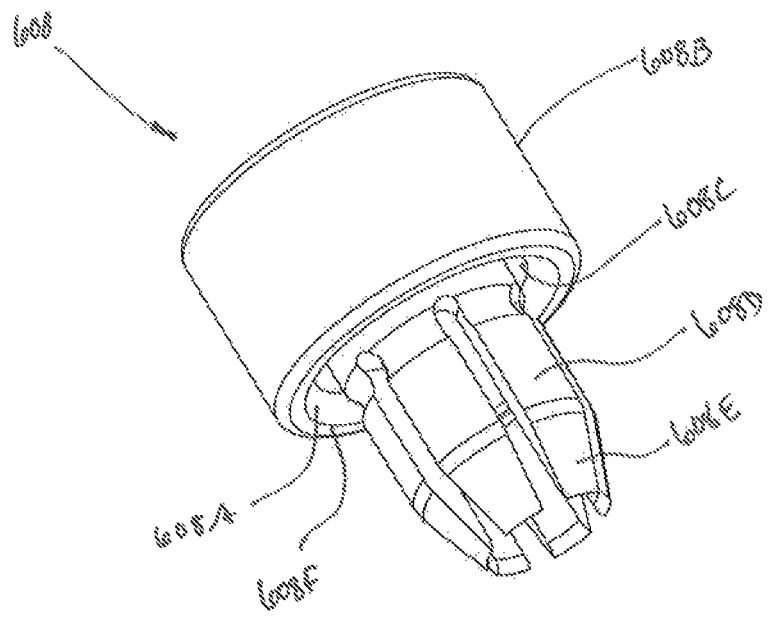
FIG. 21 is a perspective view of a retractor collar.
Figure 22:
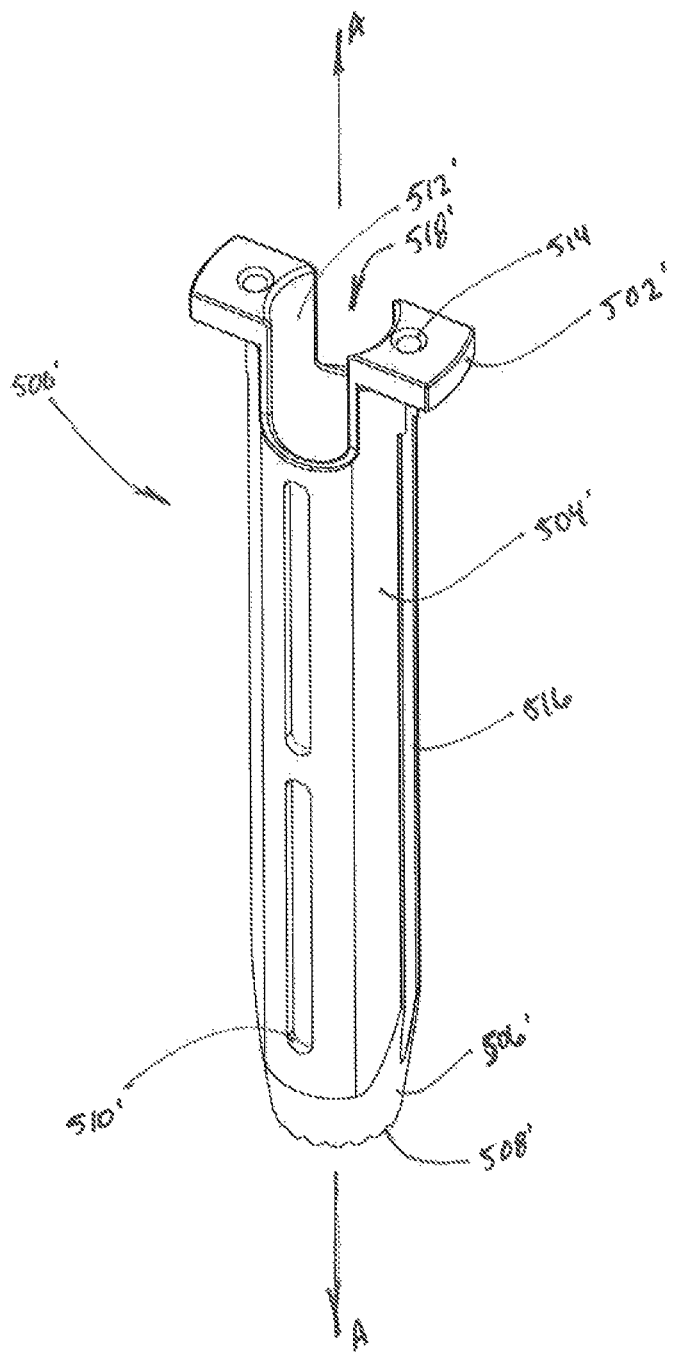
FIG. 22 is a perspective view of an outer dilator.
Figure 23A:
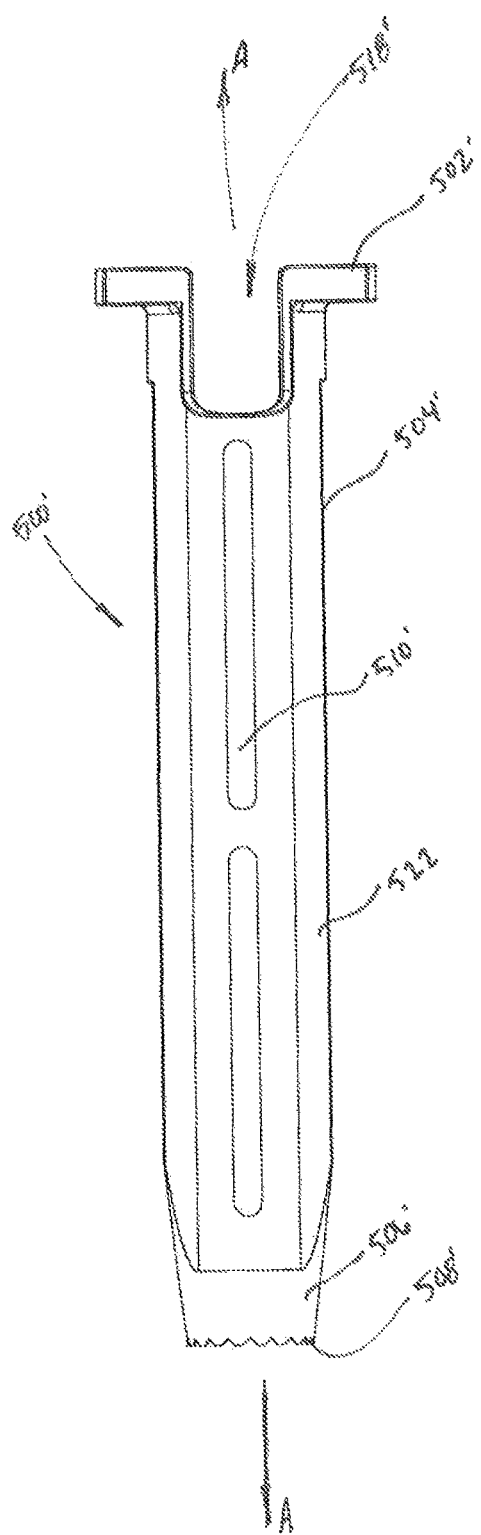
FIG. 23A is a front plan view of the outer dilator of FIG. 22.
Figure 23B:
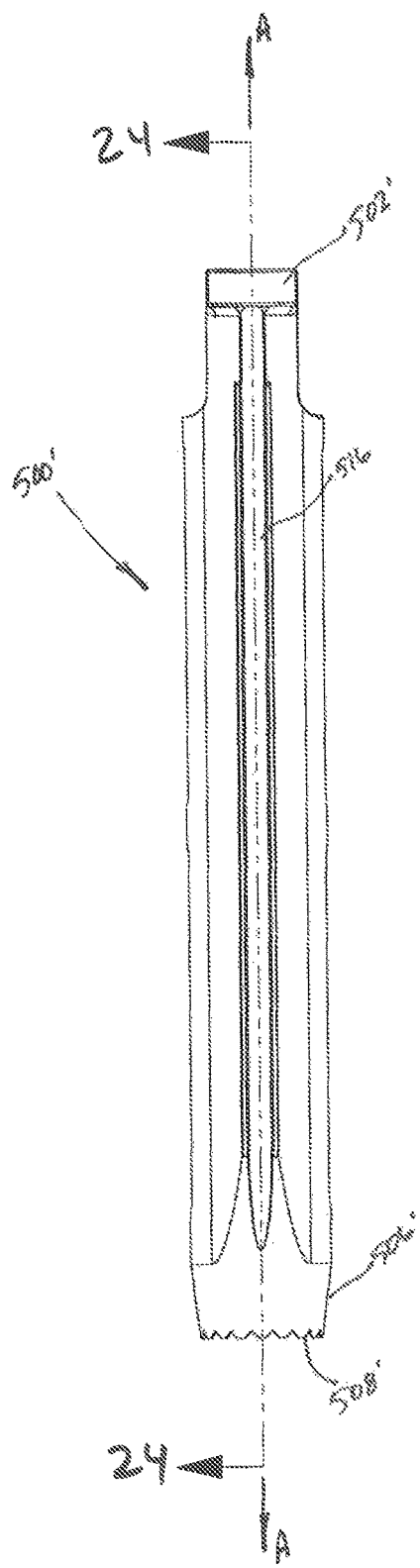
FIG. 23B is a side plan of the outer dilator of FIG. 22.
Figure 24:
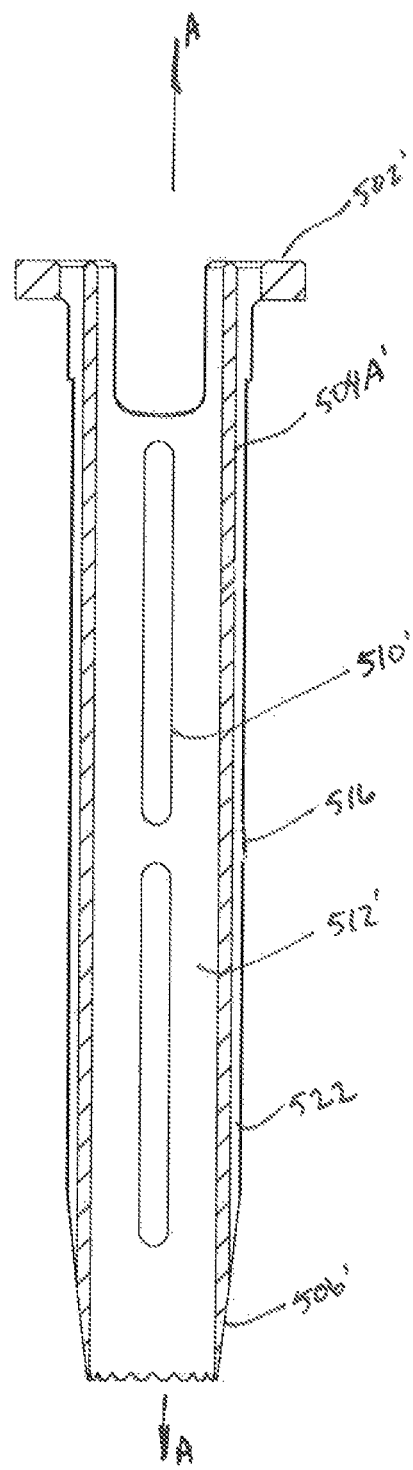
FIG. 24 is a cross-sectional view of the outer dilator of FIG. 23B, taken along section line 24-24 of FIG. 23B.
Figure 25A:
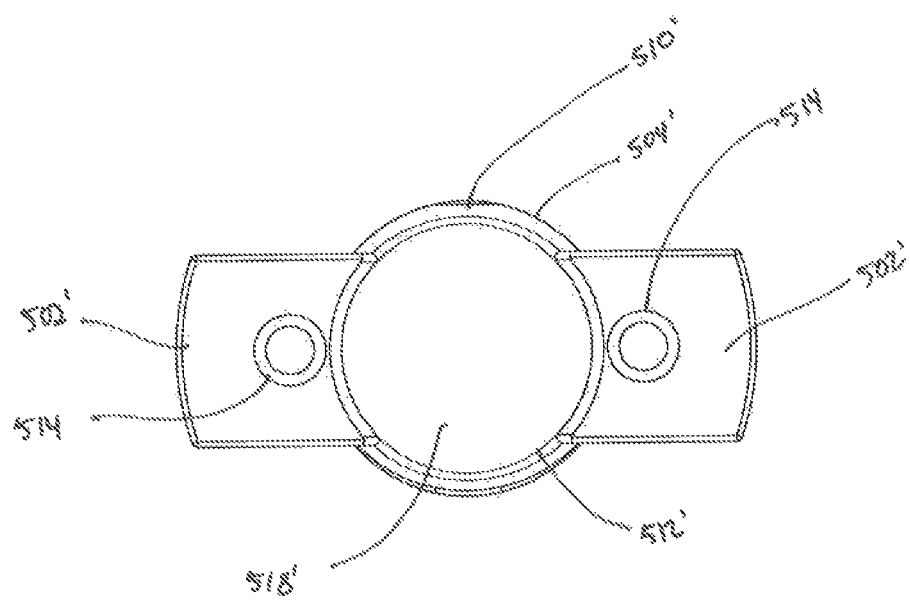
FIG. 25A is a top plan view of the outer dilator of FIG. 22.
Figure 25B:
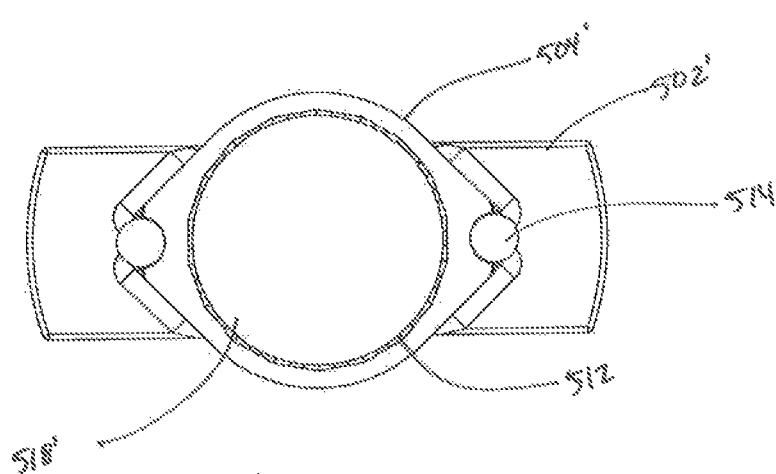
FIG. 25B is a bottom plan view of the outer dilator of FIG. 23B.

Referring to FIG. 21, the retractor collar 608 is illustrated, including an outer collar surface 608B, an inner surface 608A, a distal collar surface 608F, and collar flanges 608D. Upon insertion into the retractor 610, the proximal region of retractor 610 may be pressed against the distal collar surface 608F. The inner surface 608A thereby prevents retractor 610 from separating along retractor seams (not shown) during the surgical dilation procedure. The collar flanges 608D are dimensioned to be received by the proximal region of the retractor 610 prior to insertion into the tissue dilation system "D". The collar flanges 608D may include a tapered surface 608E which facilitates assembly of the retractor 610 and the retractor collar 608 during the dilation procedure, as is necessary.

Referring to FIGS. 22-25, another embodiment of an outer dilator is illustrated as outer dilator 500' and may include an outer tubular member 504', an inner tubular member surface 512', flange 502', and a tapered surface 506'. The flanges 502' may further include an openings 514 dimensioned to receive a temporary fixation pin 700 (see FIGS. 26A, 26B). The outer dilator 500' may further include one or more cavities 516 located along the outer tubular member 504', each cavity 516 dimensioned to receive at least a portion of temporary fixation pin 700 therealong. Additionally, protrusion 522 may be located along the outer tubular member 504' and may partially or fully enclose each cavity 516, thereby preventing the temporary fixation pin 700 from moving laterally relative to outer dilator 500' while guiding longitudinal movement of the temporary fixation pin 700.

Figure 26A:
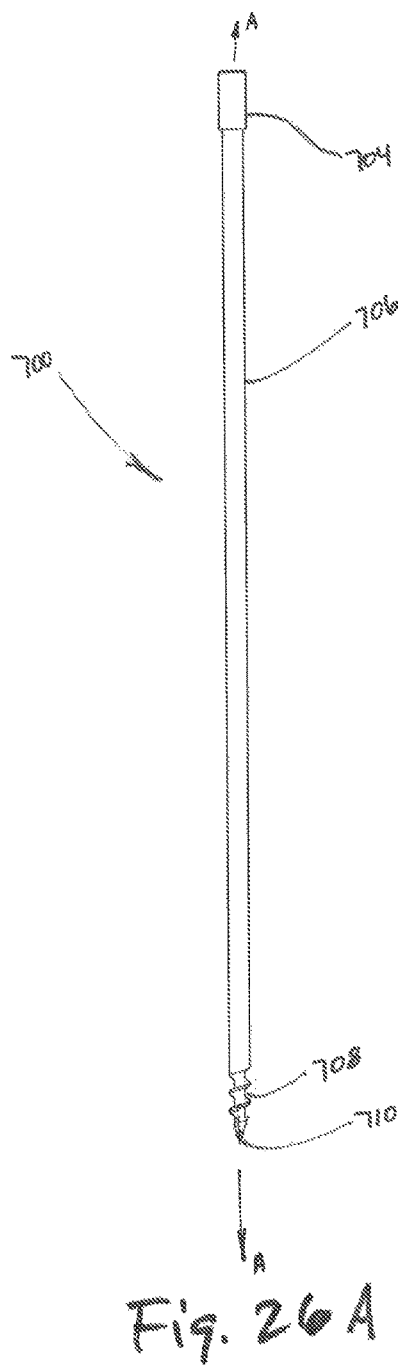
FIG. 26A is a side plan view of a temporary fastener.
Figure 26B:
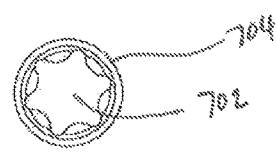
FIG. 26B is a top view of the temporary fastener of FIG. 26A.

Referring to FIGS. 26A-26B, the temporary fixation pin 700 may include a recess 702, a proximal region 704, a tubular member 706, threads 708, and a tip 710. The recess 702 may be located in a proximal region of the temporary fixation pin 700. The recess 702, as illustrated in FIG. 26B has a hexalobular shape, which permits engagement with a surgical tool, providing increased grip for application of rotational force to temporary fixation pin 700. It will be apparent to one skilled in the art that recess 702 may be shaped in a variety of different ways which permit precise transfer of rotational force from a surgical instrument (not shown) while reducing the chance of stripping the recess 702 during installation and removal.

With continued reference to FIG. 26A, a tubular member 706 traverses the longitudinal axis A-A, connecting a proximal region 704 to threads 708 and a temporary fixation pin tip 710.

Figure 27:
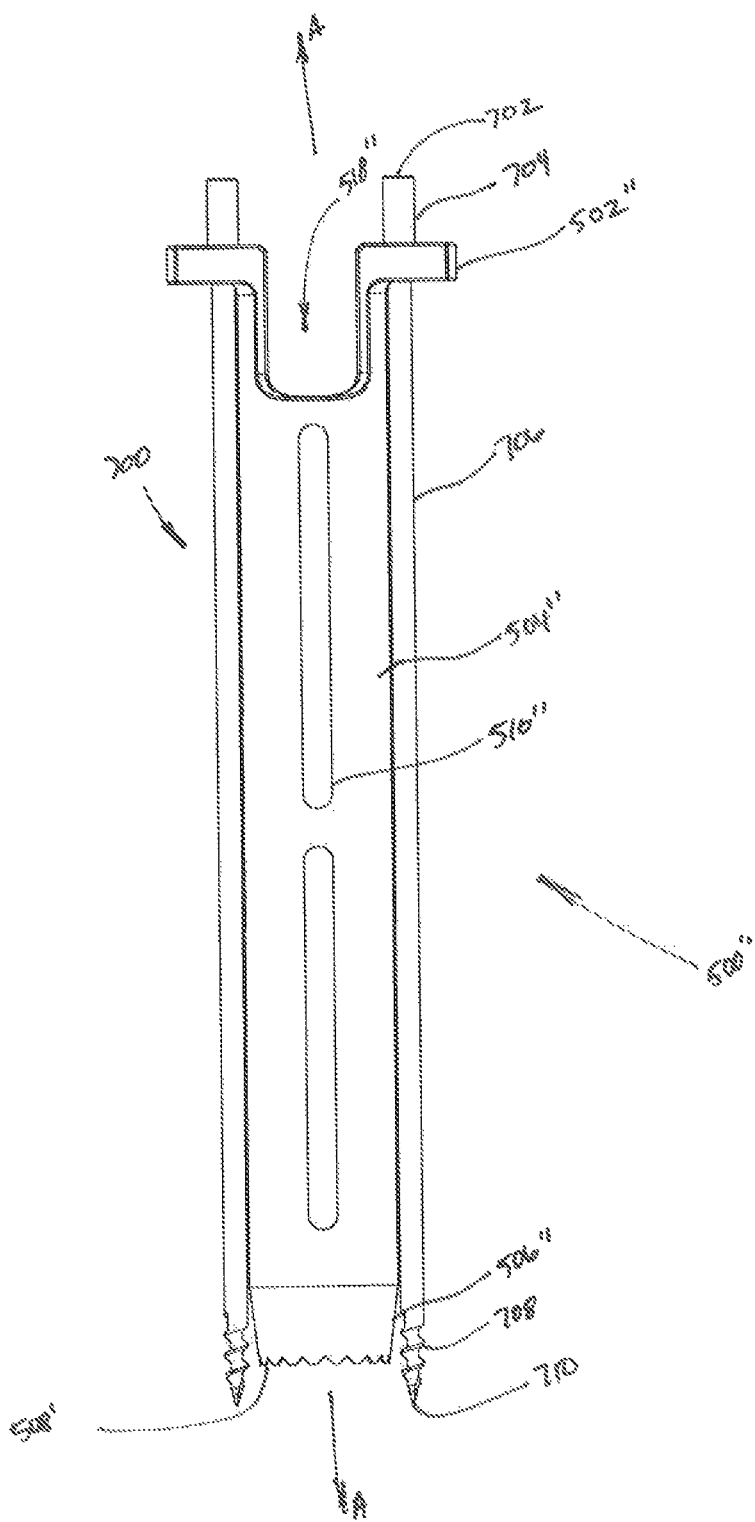
FIG. 27 is a front plan view of another embodiment of an outer dilator and the temporary fastener of FIG. 26A.

Referring to FIG. 27, another embodiment of an outer dilator is illustrated as outer dilator 500" and may include an outer tubular member 504", an inner tubular member surface 512", flange 502", and a tapered surface 506". The flanges 502" further include openings 514" dimensioned to receive a temporary fixation pin 700 (see FIGS. 26A, 26B) therethrough. The temporary fixation pin 700 of FIGS. 26A-26B is combined with outer dilator 500". During installation, the tip 710 may be advanced through the proximal region of outer dilator 500' through opening 514" located on flange 502". The temporary fixation pin 700 may subsequently be advanced along longitudinal axis A-A to be engaged with the target surface. After assembly, the temporary fixation pin 700 may maintain force against flange 502", thereby providing additional force against outer dilator 500", fixing outer dilator 500" to target tissue.

It is contemplated that a kit may be provided including the tissue dilation system "D" as disclosed herein. Additionally, a kit may include the retractor system 600 as described herein, either combined with the tissue dilation system "D" or as a stand-alone kit. In alternative kits, outer dilator 500' and/or outer dilator 500" may be included separately, or in combination with one or more temporary fixation pins 700, inner dilator 400, trocar 100, and/or handle portion 200. It is also contemplated that temporary fixation pins 700 may be included in a separate kit. Additional tools which may be useful for a clinician during the dilation procedure may be included in the described kits. The kits described in the present disclosure may be provided with sterile packaging to facilitate opening and immediate use in a sterile environment such as an operating room.

Any of the components presently disclosed may be formed of any suitable biocompatible material which is of sufficient strength to receive both the longitudinal and rotational forces necessary for the procedures described. It is contemplated that the disclosed devices may be made of materials including, but not limited to, titanium, titanium alloys, stainless steel, cobalt chrome, and nickel titanium or polymer compositions.

Persons skilled in the art will understand that the structures and methods specifically described herein and shown in the accompanying figures are non-limiting exemplary embodiments, and that the description, disclosure, and figures should be construed merely as exemplary of particular embodiments. It is to be further understood that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure, and that such modifications and variations are also included within the scope of the present disclosure. Accordingly, the subject matter of the present disclosure is not limited to what has been particularly shown and described.

What is claimed is:

1. A tissue dilation system comprising: a trocar having an elongated body with a bore extending therethrough, a distal region of the elongated body having threads for engaging bone; a stylet insertable into the bore; a first dilator having an elongated body and translatable over an outer surface of the trocar; and an outer dilator having an elongated body and translatable over an outer surface of the first dilator.

2. The tissue dilation system of claim 1, further including a handle portion configured to be removably attached to the trocar.

3. The tissue dilation system of claim 2, further including a handle portion configured to be removably attached to the first dilator.

4. The tissue dilation system of claim 1, wherein the outer dilator is configured to receive a surgical device configured to be translated within the outer dilator for engaging bone.

5. The tissue dilation system of claim 4, wherein the surgical device is a retractor assembly including a retractor, and a screw inserter assembly.

6. The tissue dilation system of claim 5, wherein the retractor assembly further includes a screw and a knob.

7. A method for dilating tissue comprising: inserting a trocar into a target surface, the trocar having a tubular member with a bore extending between proximal and distal regions thereof, the distal region including threads for engaging bone; coupling a stylet to the trocar such that a distal region of the stylet extends beyond the distal region of the trocar; contacting bone at the target surface with the distal region of the trocar; separating the stylet from the trocar; translating a first dilator over the trocar towards bone at the target surface; translating an outer dilator over the first dilator; and coupling the outer dilator to bone at the target surface.

8. The method of claim 7, further including connecting the trocar with bone at the target surface.

9. The method of claim 7, wherein translating the first dilator over the trocar includes the first dilator having a serrated edge configured to engage with a target surface.

10. The method of claim 7, wherein translating the outer dilator over the first dilator includes the outer dilator having a distal region with a serrated edge configured to engage with a target surface.

11. The method of claim 10, wherein translating the first dilator over the trocar includes the first dilator having a bore configured for slidably receiving the trocar.

12. The method of claim 11, wherein translation of the outer dilator over the first dilator includes the outer dilator having a bore configured to engage with an outer surface of the first dilator.

13. The method of claim 12, further including removably attaching a handle to either the trocar or the first dilator.

14. The method of claim 12, further including coupling the first dilator and the outer dilator prior to translating the first dilator over the trocar towards bone at the target surface.

15. The method of claim 7, further including separating the trocar from the target surface.

16. The method of claim 7, further including separating the first dilator from the target surface.

* * * * *